United States Patent [19]

Makovec et al.

[11] Patent Number: 5,922,875

[45] Date of Patent: Jul. 13, 1999

[54] AROMATIC ACID DIAMIDES WITH ANTIGASTRIN ACTIVITY, A METHOD FOR THEIR PREPARATION AND THEIR PHARMACEUTICAL USE

[75] Inventors: Francesco Makovec, Monza; Walter Peris, Milan; Lucio C. Rovati; Luigi A. Rovati, both of Monza, all of Italy

[73] Assignee: Rotta Research Laboratorium S.p.A., Milan, Italy

[21] Appl. No.: 08/981,804

[22] PCT Filed: Jun. 28, 1996

[86] PCT No.: PCT/EP96/02829

§ 371 Date: Dec. 29, 1997

§ 102(e) Date: Dec. 29, 1997

[87] PCT Pub. No.: WO97/02248

PCT Pub. Date: Jan. 23, 1997

[30] Foreign Application Priority Data

Jul. 3, 1995 [IT] Italy .................................. TO95A0554

[51] Int. Cl.[6] ...................... C07D 211/00; C07D 215/00; C07D 401/00

[52] U.S. Cl. .................. 546/16; 546/17; 546/15; 546/18; 514/278

[58] Field of Search ............... 514/278; 546/16, 546/15, 17, 18

[56] References Cited

FOREIGN PATENT DOCUMENTS

| | | |
|---|---|---|
| WO9210479 | 6/1992 | WIPO . |
| WO9321172 | 10/1993 | WIPO . |
| WO9420454 | 9/1994 | WIPO . |
| WO9507261 | 3/1995 | WIPO . |

*Primary Examiner*—D. Margaret M. Mach
*Attorney, Agent, or Firm*—Sughrue, Mion, Zinn, Macpeak & Seas, PLLC

[57] ABSTRACT

A compound represented by the general formula (I) shown below

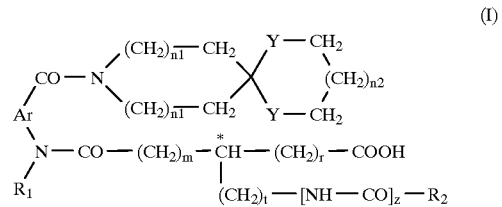

or a pharmaceutically acceptable salt thereof can be used as the active ingredient in a pharmaceutical preparation. The pharmaceutical preparation is desirable for its anti-ulcer activity, for therapeutic use against tumors sustained by gastrin and other bioactive polypeptides correlated therewith, for therapeutic use in treating disorders of the gastrointestinal tract, for the treatment of pathological conditions of the central nervous system linked to imbalances in the neural physiological levels of gastrin or other bioactive polypeptides correlated therewith, for use in the treatment and prevention of pathological eye conditions caused by surgical treatment of cataracts or chronic ocular inflammation, and for the prevention of diseases of other sensory organs.

12 Claims, No Drawings

AROMATIC ACID DIAMIDES WITH ANTIGASTRIN ACTIVITY, A METHOD FOR THEIR PREPARATION AND THEIR PHARMACEUTICAL USE

This application is a 371 of PCT/EP96/02829, filed Jun. 28, 1996.

The present invention relates to new aromatic acid amide derivatives which may be represented by the general formula (I) shown below:

$$\text{(I)} \quad \begin{array}{c} Ar-CO-N \begin{pmatrix} (CH_2)_{\overline{n1}}-CH_2 \\ (CH_2)_{\overline{n1}}-CH_2 \end{pmatrix} \begin{pmatrix} Y-CH_2 \\ Y-CH_2 \end{pmatrix} (CH_2)_{n2} \\ \overset{|}{N}-CO-(CH_2)_m-\overset{*}{CH}-(CH_2)_r-COOH \\ \overset{|}{R_1} \qquad\qquad (CH_2)_t-[NH-CO]_z-R_2 \end{array}$$

in which:

Ar is
- a phenyl group or an unsubstituted pyridyl group or a pyridyl group mono- or di-substituted with a group selected independently from $C_1$–$C_4$ alkyl, $C_1$–$C_4$ alkoxy, phenyl, cyano, nitro, amino, hydroxyl, halogens such as fluorine, chlorine, bromine, trifluoromethyl or
- a naphthyl group
- a quinolinyl group $n_1$ is selected independently from 1 and 2;

$n_2$ is selected independently from 0 (zero) and 1;

Y is selected independently from $CH_2$ and O (oxygen);

m, r and t are integers independently selected one from the others, having a value from 0 (zero) to 2;

z is 0 (zero) or 1;

$R_1$ is selected independently from H (hydrogen) and methyl $R_2$ is selected independently from a phenyl group unsubstituted or mono- or di-substituted with methyl or with chlorine, a 1- (or 2-)naphthyl, a 2-(or 3-) indolyl, a 2-(or 3-)quinolinyl group.

The configuration of the chiral centre indicated * in the general formula (I) may be, independently, D (dextro), L (laevo) or DL (racemic). Preferably the two amide groups bonded directly to Ar are in the ortho positions to each other and Ar is preferably naphthyl or the group 3,5-dimethylphenyl; Y is $CH_2$, $n_1$ is 1 and $n_2$ is 0 (zero); $R_1$ is H (hydrogen) and $R_2$ is 1-naphthyl; m and r are both 1; t and z are both 0 (zero).

The compounds of the present invention have been shown to be powerful antagonists to the gastrin receptors at the peripheral level, that is in the gastrointestinal system, and on cholecystokinin (CCK) receptors in the central nervous system (CCK-B-antagonists). It may thus be thought that they may be usable to advantage in the treatment of various illnesses in man linked to imbalances in the physiological levels of gastrin and CCK or other bioactive polypeptides correlated therewith, both in the gastrointestinal tract and the central nervous system (CNS) or other organs or systems in which these bioactive peptides play a physiological or pathological role. Thus, for example, one may foresee an advantageous use of these compounds in the treatment, at the gastrointestinal level, of illnesses linked to disturbances in motility and mucous trophism such as, for example, gastritis, peptic ulcers, colitis and certain forms of gastrointestinal tumours supported by gastrin or polypeptide hormones correlated therewith, and at the level of the CNS for treating mental disorders such as anxiety, panic attacks, psychosis, such as, for example schizophrenia, depression, anorexia etc. Another use could be in the treatment and prevention of some pathological conditions of the eye such as, for example, myosis induced during surgical treatment for cataract or chronic eye inflammation or other disorders of the sensory organs.

Pharmaceutical forms of the compounds which are the subject of the invention may be prepared by conventional techniques as, for example, tablets, capsules, suspensions, solutions and suppositories, or patches and may be administered orally, parenterally, rectally, to the eyes or transdermally or in other forms suitable for achieving the therapeutic effect, for example as solid preparations for oral use with a protracted action which allow the controlled release of the active ingredient over a period of time.

The active ingredient is administered to the patient typically in doses of from 0.01 to 10 mg/kg body weight per dose. For parenteral and ocular administration it is preferable to use a water-soluble salt of the compounds in question, such as the sodium salt or another non-toxic and pharmaceutically acceptable salt. The inactive ingredients used may be those substances commonly used in pharmaceutical preparations as eccipients, binders, aromatising compounds, dispersants, colouring agents, humectants etc.

The process for the preparation of the derivatives of the invention consists of a series of reactions including:

a) reacting the aromatic aminoacid derivatives of formula (VII):

$$\text{(VII)} \quad \begin{array}{c} Ar-COOH \\ | \\ R_1-NH \end{array}$$

in which Ar and $R_1$ have the meanings given above with a quantity of carbobenzoxy chloride (Z—Cl) under Schotten-Bauman conditions at a temperature of 0 to 15° C. to give the acid carbamates of formula (VI) (see the reaction scheme below, conversion 1);

b) amidating the compounds of formula (VI)

$$\text{(VI)} \quad \begin{array}{c} Ar-COOH \\ | \\ R_1-N-Z \end{array}$$

with an amide of formula (V):

$$\text{(V)} \quad HN \begin{pmatrix} (CH_2)_{n1}-CH_2 \\ (CH_2)_{n1}-CH_2 \end{pmatrix} \begin{pmatrix} Y-CH_2 \\ Y-CH_2 \end{pmatrix} (CH_2)_{n2}$$

in which Y, $n_1$ and $n_2$ have the meanings given above by the mixed anhydride method in an inert, anhydrous solvent at a temperature of from −5° to i+15° C. to give the amides of formula (IV) (see the reaction scheme below, conversion 2);

c) decarbobenzoxylating the compounds of formula (IV)

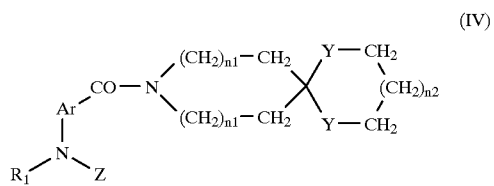
(IV)

dissolved in an inert solvent by reacting them with hydrogen at ambient temperature and pressure in the presence of a catalytically effective quantity of a hydrogenating catalyst, such as palladium, to give the basic derivatives of formula (III) (see the reaction scheme below, conversion 3);

d) reacting the basic derivatives of formula (III)

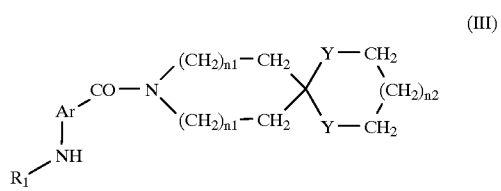
(III)

with the appropriate anhydrides of formula (II)

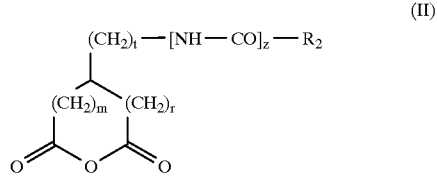
(II)

in which $R_2$, m, r, t, z and (*) have the meanings given above, in a molar ratio of from 1 to 2, in an inert solvent at a temperature of between 0° C. and the boiling point of the solvent, in the presence or absence of a tertiary base, to give the corresponding final derivatives of formula (I) according to the following reaction scheme, conversion 4.

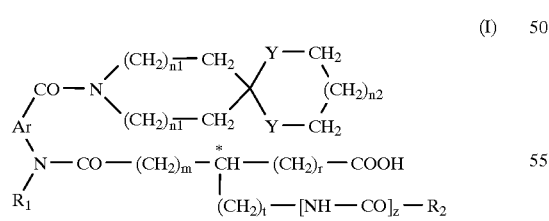
(I)

Alternatively, and preferably, the corresponding monoacid chlorides may be used instead of the anhydrides of formula (II) specifically when m and r are both 0 (zero).

The anhydrides of formula (II) are available commercially or are described in the literature or have been prepared from the corresponding acids by conventional methods.

General synthesis route (Scheme 1)

Conversion 1.

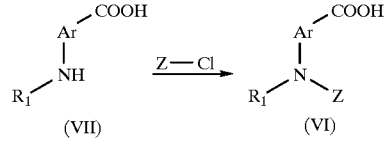

Conversion 2.

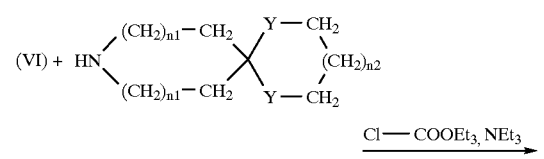
(IV)

Conversion 3.

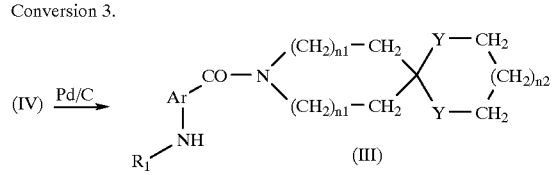

Conversion 4.

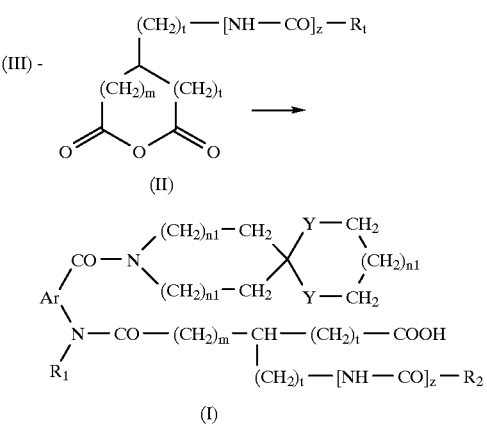
(I)

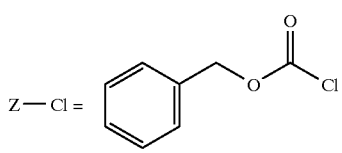

The following examples are given in order better to illustrate the invention.

EXAMPLE 1

Preparation of N-carbobenzoxy-3-amino-2-naphthoic acid 5.5 g of sodium bicarbonate (0.0655 moles) were dissolved in 60 mL of water and 5.8 g of 3-amino-2-naphthoic acid (0.0312 moles) were added. 80 mL of tetrahydrofuran were then added and the resulting solution was heated to 40° C. At this temperature a solution of 5.2 mL of benzyl chloroformate (0.0343 moles) were added dropwise. At the end of this addition, the heating was stopped and the reaction was left to proceed for twelve hours at ambient temperature. The aqueous phase was acidified with 35% HCl and the oil which separated was extracted with ethyl acetate. The organic phase was washed with water until neutral, dried and evaporated. The solid residue obtained was taken up with isopropyl ether and filtered. After drying at 50° C., 10 g of product were obtained.

Formula: $C_{19}H_{15}NO_4$. Quantitative yield. TLC (iAmOH/acetone/water 5:2:1): rf 0.64. Mp 208° C. All the intermediate compounds of formula VI were synthesised by the same procedure (see Scheme 1, conversion 1).

EXAMPLE 2

Preparation of 2-(carbamoyl-8-azaspiro[4.5]decan-8-yl)-3-N-carbobenzoxyamino naphthalene 9 g of N-carbobenzoxy-3-amino-2-naphthoic acid (0.028 moles) were dissolved in 100 mL of tetrahydrofuran. The solution was cooled to −5° C. and 4.1 mL of triethylamine (0.0294 moles) were added under agitation. The mixture was kept under agitation and a solution of 2.8 mL of ethyl chloroformate (0.0294 moles) in 10 mL tetrahydrofuran were added dropwise. At the end of this addition the mixture was kept under agitation at −5° C. for 15 minutes and then a solution of 4.7 g 8-azaspiro[4.5]decan(0.0336 moles) in 10 mL of tetrahydrofuran were added dropwise and then the mixture was left for the temperature to rise to ambient temperature and agitation was continued for one night. The precipitate was filtered off and the solvent evaporated. The oily residue obtained was dissolved in ethyl acetate and the organic phase was washed first with dilute HCl, then with dilute NaOH and finally with water until neutral. The organic phase was dried and evaporated and the solid obtained was taken up with a mixture of 1:4 isopropyl ether/hexane. The product was filtered off and dried in an oven at 50° C., giving 8 g.

Formula: $C_{28}H_{30}N_2O_3$. Yield (64%). TLC (benzene/AcOEt 7:3): rf 0.71. Mp 122° C. All the intermediate compounds of formula IV were synthesised by the same method (see Scheme 1, conversion 2).

EXAMPLE 3

Preparation of 2-(carbamoyl-8-azaspsiro[4.5]decan-8-yl)-3-amino naphthalene 3.5 g of amide (0.0079 moles; Compound of Example 2) were dissolved in 100 mL of methanol; to this solution was added a suspension of 0.5 g of palladium on carbon at 10% concentration in 5 mL of water. The resulting suspension was hydrogenated in a current of hydrogen at ambient pressure and temperature for six hours. After this period, the catalyst was filtered off and the solvent evaporated. The oil obtained was dissolved in ethyl acetate and the organic phase was washed with a saturated solution of sodium bicarbonate. The solvent was dried and evaporated and the oily residue was made friable with hexane; after filtration and drying, 2 g of the solid product were recovered.

Formula: $C_{20}H_{24}N_2O$. Yield 82%. TLC (benzene/AcOEt 7:3): rf 0.16. Mp 114° C. All the intermediate compounds of formula III were synthesised by the same method (see Scheme 1, conversion 3).

EXAMPLE 4

Preparation of 3-(1-naphthyl) glutaric anhydride 20 g of 3-(1-naphthyl) glutaric acid (0.0774 moles) prepared by the method described by Hey et al [J. Chem. Soc. 1949, 3177–81] were suspended in 400 mL of isopropyl ether. 36.5 mL of acetic anhydride (0.387 moles) were added and the suspension, well agitated, was heated under reflux for three hours. At the end of this time, the mixture was cooled to ambient temperature and the precipitate filtered off and washed well with isopropyl ether. After drying at 60° C. under vacuum, 13.9 g of the product were recovered.

Formula: $C_{15}H_{12}O_3$. Yield 75%. Mp 166° C.

EXAMPLE 5

Compound 13 of Table 1

Preparation of 3-(DL)-(1-naphthyl)-5-[2'-carbamoyl(8-azaspiro[4.5]dec-8-yl)]-3'-naphthylamino]-5-oxopentanoic acid 1.7 g of amine (0.0055 moles; Compound of Example 3) and 1.3 g of 3-(1-naphthyl) glutaric anhydride (0.0055 moles) were dissolved in 70 mL of dioxan. The solution was refluxed under agitation for five hours. It was then cooled to ambient temperature and the solvent was evaporated; the residue was dissolved in ethyl acetate and the organic phase was washed with 2N HCl and with water until neutral. The solution was dried and evaporated and the solid obtained was taken up with isopropyl ether and filtered; after drying at 50° C., 2.2 g of product were obtained.

Formula: $C_{35}H_{36}N_2O_4$. Yield 75%. HPLC: rt 10.3 min. Mp 189° C. HPLC conditions: Econosphere C18 column, length 25 cm, eluent $KH_2PO_4$ 0.01 M/MeOH 25/75 (pH 2.85), flow 0.88 mL/min, UV detector at 239 nm. All the compounds of formula I were synthesised by the same method (see Scheme 1, conversion 4).

Table 1 below gives several derivatives of formula I according to the invention obtained in this manner together with several physico-chemical identifying characteristics.

TABLE 1

Compounds of formula

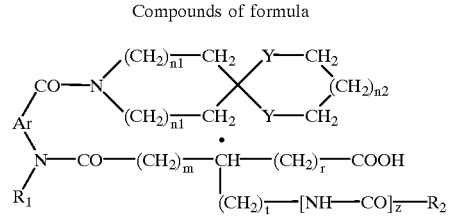

| Compound | Formula | Ar | Position of —CO—N on Ar | Position of NR₁—CO on Ar | R1 | R2 | Y | n1 | n2 | m | r | t | z | Melting point (° C.) | HPLC (rt) min |
|---|---|---|---|---|---|---|---|---|---|---|---|---|---|---|---|
| 1 | $C_{33}H_{34}N_2O_4$ | phenyl | 1 | 2 | H | 1-naphthyl | $CH_2$ | 1 | 0 | 1 | 1 | 0 | 0 | 173 | 7.17 |

TABLE 1-continued

Compounds of formula $$\text{Ar}-\text{CO}-\text{N}\begin{pmatrix}(CH_2)_{\overline{n1}}-CH_2 & Y-CH_2\\ (CH_2)_{\overline{n1}}-CH_2 & Y-CH_2\end{pmatrix}(CH_2)_{n2}$$

$$\text{N}-\text{CO}-(CH_2)_{\overline{m}}-\underset{|}{\text{CH}}-(CH_2)_{\overline{r}}-\text{COOH}$$
$$\underset{R_1}{\phantom{N}}\qquad\qquad (CH_2)_{\overline{t}}-[\text{NH}-\text{CO}]_{\overline{z}}-R_2$$

| Compound | Formula | Ar | Position of —CO—N on Ar | Position of NR₁—CO on Ar | R1 | R2 | Y | n1 | n2 | m | r | t | z | Melting point (° C.) | HPLC (rt) min |
|---|---|---|---|---|---|---|---|---|---|---|---|---|---|---|---|
| 2 | C₃₂H₃₆N₂O₄ | 3-methylphenyl(a) | 1 | 2 | H | 1-naphthyl | CH₂ | 1 | 0 | 1 | 1 | 0 | 0 | 163 | 7.31 |
| 3 | C₃₂H₃₆N₂O₄ | 5-methylphenyl | 1 | 2 | H | 1-naphthyl | CH₂ | 1 | 0 | 1 | 1 | 0 | 0 | 110 | 8.47 |
| 4 | C₃₃H₃₈N₂O₄ | 3,5-dimethyl-phenyl | 1 | 2 | H | 1-naphthyl | CH₂ | 1 | 0 | 1 | 1 | 0 | 0 | 192 | 8.32 |
| 5 | C₃₁H₃₃ClN₂O₄ | 3-chlorophenyl | 1 | 2 | H | 1-naphthyl | CH₂ | 1 | 0 | 1 | 1 | 0 | 0 | 239 | 7.07 |
| 6 | C₃₁H₃₃ClN₂O₄ | 4-chlorophenyl | 1 | 2 | H | 1-naphthyl | CH₂ | 1 | 0 | 1 | 1 | 0 | 0 | 220 | 9.06 |
| 7 | C₃₁H₃₃ClN₂O₄ | 5-chlorophenyl | 1 | 2 | H | 1-naphthyl | CH₂ | 1 | 0 | 1 | 1 | 0 | 0 | 182 | 9.92 |
| 8 | C₃₁H₃₃FN₂O₄ | 5-flurophenyl | 1 | 2 | H | 1-naphthyl | CH₂ | 1 | 0 | 1 | 1 | 0 | 0 | 117 | 7.57 |
| 9 | C₃₂H₃₆N₂O₅ | 3-methoxyphenyl | 1 | 2 | H | 1-naphthyl | CH₂ | 1 | 0 | 1 | 1 | 0 | 0 | 182 | 7.47 |
| 10 | C₃₃H₃₈N₂O₆ | 4,5-dimethoxy-phenyl | 1 | 2 | H | 1-naphthyl | CH₂ | 1 | 0 | 1 | 1 | 0 | 0 | 119 | 6.48 |
| 11 | C₃₁H₃₆N₂O₄ | phenyl | 1 | 3 | H | 1-naphthyl | CH₂ | 1 | 0 | 1 | 1 | 0 | 0 | 200 | 7.24 |
| 12 | C₃₂H₃₅N₃O₅ | phenyl | 1 | 3 | H | 1-naphthyl | CH₂ | 1 | 0 | 0 | 2 | 0 | 1 | 151 | 6.15 |
| 13 | C₃₅H₃₆N₂O₄ | naphthyl | 2 | 3 | H | 1-naphthyl | CH₂ | 1 | 0 | 1 | 1 | 0 | 0 | 189 | 10.3 |
| 14 | C₃₃H₃₂N₂O₆ | naphthyl | 2 | 3 | H | 1-naphthyl | oxygen | 1 | 0 | 1 | 1 | 0 | 0 | 209 | 5.22 |
| 15 | C₃₀H₃₈N₂O₄ | 3,5-dimethyl-phenyl | 1 | 2 | H | 2-methyl-phenyl | CH₂ | 1 | 0 | 1 | 1 | 0 | 0 | 205 | 7.35 |
| 16 | C₂₉H₃₅ClN₂O₄ | 3,5-dimethyl-phenyl | 1 | 2 | H | 3-chloro-phenyl | CH₂ | 1 | 0 | 1 | 1 | 0 | 0 | 203 | 7.88 |
| 17 | C₃₂H₃₆N₂O₄ | phenyl | 1 | 2 | CH₃ | 1-naphthyl | CH₂ | 1 | 0 | 1 | 1 | 0 | 0 | 119 | 7.55 |
| 18 | C₃₆H₃₈N₂O₄ | naphthyl | 2 | 3 | H | 1-naphthyl | CH₂ | 1 | 1 | 1 | 1 | 0 | 0 | 210 | 12.6 |

(a): ammonium salt

Description of the Pharmacological Activity

1) Anti-cholecystokynin activity (anti-CCK-B) in vitro

The capacity of the compounds which are the subject of the invention to interact with the central CCK-B receptor was evaluated with the use of [3-H][N-methyl-N-leucine] CCK-8. The binding was shown to be selective for the CCK-B receptors, having an affinity about 4000 times higher for the receptors of the cortex (CCK-B) than those of the pancreas (CCK-A) in guinea pigs [Knapp et.al; J.Pharmacol. and Exp. Therap 255 (3) (1990), 1278–1286]. The cerebral cortices of male albino guinea pigs were therefore used, the method given above being followed with slight modifications [Makovec et al.; Bioorganic & Med. Chem. Letters 3 (5)(1993), 861–866] so as to give a membrane content corresponding to about 300 mcg of protein/mL. The results obtained are given in Table 2 which shows the $IC_{50}$ values, that is, the concentration (in μmoles/liter) of antagonist capable of displacing 50% of the [3-H][N-methyl-N-leucine]CCK-8 from the receptor, for several of the compounds of the invention.

TABLE 2

Inhibition of the binding of ($^3$H)-[N-Methyl-N-leucine]-CCK-8 to the cortical membrane in guinea pigs

| Compound | $IC_{50} \times 10^{-8}$ M | Compound | $IC_{50} \times 10^{-8}$ M |
|---|---|---|---|
| 1 | 55.2 | 12 | >100 |
| 3 | 18.8 | 13 | 22.5 |
| 4 | 2.4 | 14 | 108 |
| 6 | 124.2 | 16 | 39.5 |
| 10 | 82.0 | 17 | >100 |
| 11 | >100 | 18 | 66.1 |
| | | Pentagastrin | 0.3 |

From the data given in Table 2 it is seen that several of the compounds of the invention are powerful inhibitors of the binding of [N-methyl-N-leucine]-CCK-8 to the receptors of the cortical membrane in guinea pigs. Thus, for example, the compound 4, having an $IC_{50}$ of $2.4 \times 10^{-8}$ M, is only 8 times less active than the specific antagonist, pentagastrin, on this experimental model.

2) Anti-gastrin activity (peripheral) in rabbit gastric mucosa cells in vitro

The parietal cells of the gastric mucosa are responsible for the secretion of HCl. They present specific membrane receptors which may be activated by gastrin and which have been defined as type-B cholecystokynin (CCK-B) or gastrin receptors.

Since it has been observed that the activation of the CCK-B receptors by gastrin results in a raising of the levels of cytosolic calcium ions, a technique has been used for measuring the increase in intracellular calcium induced by gastrin in the presence and absence of the compounds which are the subject of the invention, as an index of the anti-gastrin activity of the compounds themselves.

Suspensions ($0.8 \times 10^6$/ml) of rabbit gastric mucosa cells were prepared by conventional techniques with the use of collagenase and pronase as digestive enzymes; the estimation of the $[Ca^{2+}]_i$ values, basal or achieved after stimulation of the cell system was carried out in accordance with Grynkiewicz et al [J.Biol.Chem 260 (1985), 3440]. In the control samples the cells were stimulated with $5 \times 10^{-8}$ gastrin while in the samples in which the effect of the compounds in question was evaluated, the cells were incubated therewith before stimulation with gastrin. The results are expressed as percentage increases in $[Ca^{2+}]_i$ with respect to the control value. The anti-gastrin activity of the compounds was expressed as the $IC_{50}$ value, that is, the concentration (in μmoles/liter) at which the response to the stimulus induced by the gastrin was reduced by 50%. The results thus obtained for several compounds of the invention are given in Table 3 which also gives an index formed from the ratio between the peripheral anti-gastrin activity just described and the displacement activity derived from the study of binding to the cortical receptors of guinea pigs described above.

TABLE 3

Inhibition of the increase of cytosolic calcium induced by gastrin in rabbit gastric mucosa cells.

| Compound | $IC_{50} \times 10^{-8}$ M |
| --- | --- |
| 1 | 10.2 |
| 3 | 3.0 |
| 4 | 0.4 |
| 6 | 14.0 |
| 10 | >30 |
| 11 | 117 |
| 13 | 3.7 |
| 16 | 8.2 |
| 18 | 10.5 |

From the results given in Table 3 it is seen that several of the compounds of the invention are extremely powerful inhibitors of the increase in cytosolic calcium induced by gastrin in rabbit gastric mucosa cells.

The peripheral anti-gastrin activity essentially accords well with the anti-gastrin activity obtained centrally from the binding studies illustrated previously in Table 2. In fact, the compound 4 is also, in this case, the most powerful of the compounds described, exhibiting an $IC_{50}$ value of 4 nM. Generally the compounds in question display anti-gastrin activity on this model at concentrations 2–8 times less than those obtained centrally.

3. In vivo gastric anti-secretory activity in the rat

The gastric anti-secretory activity of the compounds of the invention, displayed through the anti-gastrin mechanism as shown by the in vitro experiments previously described, was also determined in vivo in the anaesthetised rat. Gastric secretion was stimulated by pentagastrin and the method of Lai [Gut 5, (1964), 327–341] was used with slight modifications [Makovec et al, J.Med.Chem. 35 (1992), 28–38].

Pentagastrin dissolved in physiological saline was perfused for 120 minutes at a rate of 30 mcg/kg/h. After 60 minutes of perfusion (basal stimulation), the product to be tested was administered intravenously (I.V.) in bolus form, perfusion of the stimulant continuing for the remaining 60 minutes. The activity of the product was evaluated as the percentage reduction in acid secreted after the administration of the product with respect to the basal acidity measured in the first 60 minutes, during which time only pentagastrin was present.

The antagonists tested were administered at different doses in such a way as to enable the $ID_{50}$ to be calculated, that is, the dose (in mg/kg I.V.) capable of inhibiting the effect of pentagastrin by 50%.

The results obtained in this way, expressed as the $ID_{50}$, are given in the following table (Table 4).

TABLE 4

Antagonist activity ($ID_{50}$ mg/kg I.V.) to acid secretion induced by pentagastrin (30 mg/kg/h in the rat

| Compound | Activity ($ID_{50}$) mg/kg |
| --- | --- |
| 1 | 4.9 |
| 4 | 0.2 |
| 5 | 2.6 |
| 11 | 9.7 |
| 12 | IN (>10) |
| 13 | 1.0 |
| 14 | 7.9 |
| CR 2194 | 11.0 |
| Cimetidine | 2.5 |

From the data reported in Table 4 it can be seen that many of the compounds of the invention show powerful antagonist activity to gastric acid secretion caused be pentagastrin in vivo in the rat.

Thus, for example, compounds 4 and 13, which in this experiment, are shown to be approximately 10–50 times more powerful than the CCK-B antagonist reference compound CR 2194 and approximately 2–10 times more powerful than the $H_2$ antagonist cimetidine.

The gastric anti-secretory activity of these compounds is linked specifically to their anti-gastrin activity. In fact, they have no anti-cholinergenic or antihistamine (anti-$H_2$) activity, being therefore completely inactive in the experimental model described above when used as a carbachol (30 mcg/kg/h) or histamine (2.3 mg/kg/h) stimulant.

4) Anti-cholecystokynin activity (anti-CCK-A)

In order to test the hypothesis that the compounds in question are specific CCK-B antagonists, several of the more active compounds illustrated in Tables 2 and 3 were also tested for any CCK-A antagonist activity. The experimental model used was the guinea pig gall bladder stimulated in vitro by CCK-8 according to the method described by Makovec et al. [(Arzneim. Forsch/Drug. Res. 35 (7), 1048–1051 (1985)].

None of the compounds tested displayed any anti-CCK-A activity more powerful than $1 \times 10^{-6}$ M.

If these activities are compared with the anti-CCK-B activities illustrated previously in Table 2, it may be concluded that the compounds in question are specific antagonists for the CCK-B receptor, the more powerful compounds, such as the compound 4, exhibiting an affinity at least 300 times higher for the gastrin receptor (CCK-B) than for the cholecystokynin receptor (CCK-A).

5) Anxiolytic activity

Among the possible therapeutic activities of the compounds in question on the central nervous system, linked to imbalances in the physiological neural levels of gastrin or other peptides correlated therewith, their potential anxiolytic activity appears particularly interesting.

It has in fact recently been postulated that the central CCK-B receptor plays an important role in anxiety. This accords with studies also carried out in man which have shown that the central CCK-B mechanisms have an important function in the mediation of panic attacks [Bradwejn, J.et al; J.Psychopharmacology 6 (1992), 345]. In order to confirm this hypothesis, the anxiolytic activities of several of the most powerful CCK-B antagonists of the invention were evaluated by the method of the "elevated plus-maze"

in rats, carried out in accordance with Pellow et al. [J. of Neurosc. Meth. 14(1985), 149–167]. A labyrinth was used in which the length of the cross arm was about 45 cm placed at a height from the ground of 70 cm. On this experimental model, a compound having anxiolytic activity produces a percentage increase in the stay time in the open arms and a percentage increase in the number of entries into the open arms.

The results obtained are given in Table 5 below where the activities obtained with different doses of the compound 4 administered intraperitoneally (IP) are given in comparison with a group of animals treated with a physiological saline in the same way.

TABLE 5

Anxiolytic activity in the rat in the "Plus Maze" Test

| Compound | Dose mg/kg I.P. | No. Animals | Entries to open arm/ total entries (%) | % Effect Vs controls | Time in open arm/ total time (%) | % Effect VS controls |
|---|---|---|---|---|---|---|
| Control | — | 16 | 30.5 | — | 19.1 | — |
| Compound 4 | 0.03 | 16 | 36.4 | 19.3 | 21.1 | 10.4 |
| " | 0.3 | 16 | 42.5(*) | 39.3 | 28.2(*) | 47.9 |
| " | 3.0 | 16 | 34.0 | 11.5 | 19.9 | 4.2 |

(*): Duncan test: p < 0.05 vs control group

From an examination of Table 5 it is seen that the compound 4 displays an anxiolytic effect.

It is in fact seen that, in the dose range 0.03–3 mg/kg I.P., the compound increases the percentage number of entries into the open arm over the total number of entries compared with the controls.

At the central dose used, that is 0.3 mg/kg I.P., the compound 4 also increases the percentage stay time in the open arms; this increase is significant compared with the group of control animals treated with saline.

The anxiolytic response displayed by the compound 4 has a bell profile typical of compounds which act on the central nervous system.

We claim:

1. A compound represented by the general formula (I) shown below $$\begin{array}{c} \text{(CH}_2)_{\overline{n1}}\text{—CH}_2 \quad Y\text{—CH}_2 \\ \text{CO—N} \diagdown \diagup \diagdown \\ \diagup \quad \diagdown \diagup \quad (\text{CH}_2)_{n2} \\ \text{Ar} \quad (\text{CH}_2)_{\overline{n1}}\text{—CH}_2 \quad Y\text{—CH}_2 \\ \diagdown \\ \text{N—CO—(CH}_2)_m\text{—}\overset{*}{\text{CH}}\text{—(CH}_2)_r\text{—COOH} \\ \diagup \quad | \\ R_1 \quad (\text{CH}_2)_t\text{—[NH—CO]}_z\text{—R}_2 \end{array}$$

in which:

Ar is
an unsubstituted phenyl group or an unsubstituted pyridyl group or a phenyl or a pyridyl group mono- or di-substituted with a group selected independently from $C_1$–$C_4$ alkyl, $C_1$–$C_4$ alkoxy, phenyl, cyano, nitro, amino, hydroxyl, halogens, trifluoromethyl or
a naphthyl group or
a quinolinyl group;

$n_1$ is selected independently from 1 and 2;

$n_2$ is selected independently from 0 (zero) and 1;

Y is selected independently from $CH_2$ and O (oxygen);

m, r and t are integers whose values independently range from 0 (zero) to 2;

z is 0 (zero) or 1;

$R_1$ is selected independently from H (hydrogen) and methyl;

$R_2$ is selected independently from a phenyl group unsubstituted or mono- or di-substituted with methyl or with chlorine, a 1-(or 2-) naphthyl, a 2-(or 3-) indolyl, and a 2-(or 3-) quinolinyl group;

the configuration of the chiral center indicated * in the general formula (I) being, independently, D (dextro), L (laevo) or DL (racemic)

or its salt.

2. A compound according to claim 1, wherein the two amide groups bonded directly to Ar are in the ortho position to each other and Ar is the naphthyl group or the group 3, 5-dimethylphenyl; Y is $CH_2$, $n_1$ is 1 and $n_2$ is 0 (zero) or 1; $R_1$ is H (hydrogen) and $R_2$ is 1-naphthyl; m and r are both 1; t and z are both 0 (zero).

3. A compound according to claim 1 of general formula (I) in which Ar is the group 3, 5-dimethylphenyl and the two amide groups bonded directly to the 3, 5-dimethylphenyl group are in the ortho position to each other, $n_1$ is 1, $n_2$ is 0 (zero) or 1, Y is $CH_2$, $R_1$ is H, m and r are both 1, t and z are both 0 (zero), $R_2$ is the group 1-naphthyl and the stereochemistry of the chiral center indicated (*) in the general formula (I) is D (dextro), L (laevo) or DL (racemic).

4. A compound according to claim 1 of general formula (I) in which Ar is the naphthyl group and the two amide groups bonded directly thereto are in the ortho position to each other, $n_1$ is 1, $n_2$ is 0 (zero) or 1, Y is $CH_2$, $R_1$ is H, m and r are both 1, t and z are both 0 (zero), $R_2$ is the group 1-naphthyl and the stereochemistry of the chiral center indicated (*) in the general formula (I) is D (dextro), L (laevo) or DL (racemic).

5. A pharmaceutical preparation including at least one compound of claim 1 or a pharmaceutically acceptable salt thereof as the active ingredient.

6. A pharmaceutical preparation according to claim 5 for therapeutic use as a function of its anti-ulcer activity, where the at least one compound or pharmaceutically acceptable salt thereof is present in an amount sufficient to provide a pharmacological anti-ulcer effect.

7. A pharmaceutical preparation according to claim 5 for therapeutic use against tumors sustained by gastrin and other bioactive polypeptides correlated therewith, where the at least one compound or pharmaceutically acceptable salt thereof is present in an amount sufficient to provide a pharmacological effect against said tumors.

8. A pharmaceutical preparation according to claim 5 for therapeutic use in treating disorders of the gastrointestinal tract, where the at least one compound or pharmaceutically acceptable salt thereof is present in an amount sufficient to provide a pharmacological effect in treating said disorders.

9. A pharmaceutical preparation according to claim 5 for the treatment of pathological conditions of the central nervous system linked to imbalances in the neural physiological levels of gastrin or other bioactive polypeptides correlated therewith, where the at least one compound or pharmaceutically acceptable salt thereof is present in an amount sufficient to provide a pharmacological effect in treating said pathological conditions.

10. A pharmaceutical preparation according to claim 5 for use in the treatment and prevention of pathological eye conditions caused by surgical treatment of cataracts or chronic ocular inflammation or for the prevention of diseases of other sensory organs related to the mechanism of the action of the compounds of claim 1, where the at least one compound or pharmaceutically acceptable salt thereof is present in an amount sufficient to provide a pharmacological effect in treating and preventing said pathological eye conditions or for preventing said diseases of other sensory organs.

11. A pharmaceutical preparation according to claim 5 further including pharmaceutically acceptable inactive ingredients selected from the group consisting of vehicles, binders, aromatizers, dispersants, preservatives, humectants and mixtures thereof or ingredients which facilitate transdermal absorption or which allow the controlled release of the active substance over time.

12. A method for the preparation of a derivative of general formula (I) in which Ar, $n_1$, $n_2$, Y, m, r, t, z, $R_1$, and $R_2$ have the meanings given in claim 1 and in which the substituents on the chiral center indicated (*) have the D (dextro), L (laevo), or DL (racemic) configuration, which includes the steps of:

a) reacting the aromatic aminoacid derivatives of formula (VII):

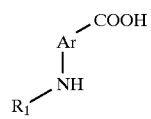

in which Ar and $R_1$ have the meanings given above with a quantity of carbobenzoxy chloride (Z—Cl) under Schotten-Bauman conditions at a temperature of 0 to 15° C. to give the acid carbonates of formula (VI);

b) aminating the compounds of formula (VI)

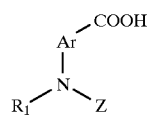

with an amino of formula (V)

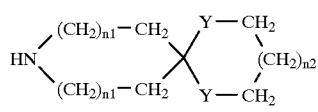

in which Y, $n_1$ and $n_2$ have the meanings given above by the mixed anhydride method in an inert, anhydrous solvent at a temperature of from −5° to I+15° C. to give the compounds of formula (IV);

c) removing the protective carbobenzoxy group from the compounds of formula (IV)

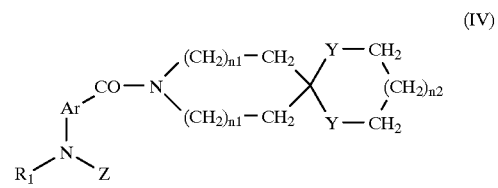

dissolved in an inert solvent by reacting them with hydrogen at ambient temperature and pressure in the presence of a catalytically effective quantity of a hydrogenating catalyst to give the basic derivatives of formula (III);

d) reacting the basic derivatives of formula (III)

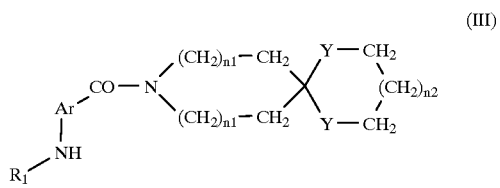

with the appropriate anhydrides of formula (II)

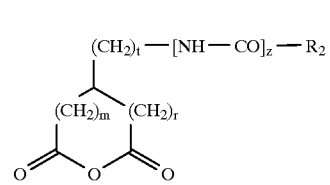

in which $R_2$, m, r, t, z and (*) have the meanings given above, in a molar ratio of from 1 to 2, in an inert solvent at a temperature between 0° C. and the boiling point of the solvent, in the presence or absence of a tertiary base, and recovering the corresponding final derivatives of formula (I) from the reaction mass as such or as pharmaceutically acceptable salts and purifying them by conventional methods,

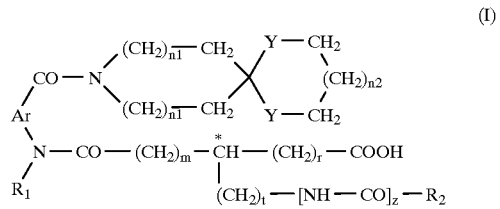

or alternatively, using the corresponding monoacid chlorides instead of the anhydrides of formula (II) and specifically when m and r are both 0 (zero).

* * * * *